US008554304B2

(12) United States Patent
Vangdal

(10) Patent No.: US 8,554,304 B2
(45) Date of Patent: Oct. 8, 2013

(54) MRI COMPATIBLE VISUAL SYSTEM THAT PROVIDES HIGH RESOLUTION IMAGES IN AN MRI DEVICE

(75) Inventor: Vegard Vangdal, Bergen (NO)

(73) Assignee: Nordicneurolab AS, Bergen (NO)

( * ) Notice: Subject to any disclaimer, the term of this patent is extended or adjusted under 35 U.S.C. 154(b) by 924 days.

(21) Appl. No.: 11/921,909

(22) PCT Filed: Jun. 7, 2006

(86) PCT No.: PCT/NO2006/000211
§ 371 (c)(1),
(2), (4) Date: Dec. 4, 2008

(87) PCT Pub. No.: WO2006/132542
PCT Pub. Date: Dec. 14, 2006

(65) Prior Publication Data
US 2009/0093705 A1  Apr. 9, 2009

(30) Foreign Application Priority Data
Jun. 10, 2005  (NO) .................................. 20052834

(51) Int. Cl.
A61B 5/055  (2006.01)
G09G 5/00  (2006.01)
H04N 9/47  (2006.01)

(52) U.S. Cl.
USPC ................................ 600/418; 345/81; 348/78

(58) Field of Classification Search
None
See application file for complete search history.

(56) References Cited

U.S. PATENT DOCUMENTS

| 4,852,500 | A | | 8/1989 | Ryburg et al. | |
| 5,134,373 | A | * | 7/1992 | Tsuruno et al. | ................ 324/309 |
| 5,339,813 | A | | 8/1994 | DeYoe et al. | |
| 5,412,419 | A | * | 5/1995 | Ziarati | ............................ 348/61 |
| 5,526,814 | A | | 6/1996 | Cline et al. | |
| 5,627,902 | A | * | 5/1997 | Ziarati | .......................... 381/385 |

(Continued)

FOREIGN PATENT DOCUMENTS

| DE | 38 44 482 | | 2/1990 |
| DE | 20105959 U1 | * | 9/2001 |
| JP | 2003-190112 | | 7/2003 |
| WO | 2005/119284 | | 12/2005 |

OTHER PUBLICATIONS

Senso Motoric Instruments "iView X(TM) MRI-LR" Product Flyer, 2010, 2 pages.*
English abstract of JP 2003-190112 dated Jul. 8, 2003.

(Continued)

Primary Examiner — Long V. Le
Assistant Examiner — Angela M Hoffa
(74) Attorney, Agent, or Firm — Ladas & Parry LLP

(57) ABSTRACT

An apparatus for providing high resolution images to patients positioned in a magnetic resonance imaging (MRI) device. The MRI device comprises a head coil arranged to surround a patient's head and to provide MRI images thereof, the apparatus comprising units for receiving video or picture image signals from an external source. The apparatus further comprises units for displaying a video or picture image, the display units being arranged in a housing, the housing being suspended in an arm comprising at least two successive members. A joint is between the housing and the adjacent member, a joint or joints are between the successive members, and a joint is between an attachment element for attaching the apparatus to the head coil, or other part of the MRI device, and the member adjacent to the coil attachment element, each being hinged to allow rotation of the joints.

14 Claims, 5 Drawing Sheets

(56) References Cited

U.S. PATENT DOCUMENTS

| | | |
|---|---|---|
| 5,706,070 A | 1/1998 | Reich et al. |
| 5,794,621 A * | 8/1998 | Hogan et al. ............ 600/407 |
| 5,861,865 A * | 1/1999 | Anand et al. ............ 345/658 |
| 5,864,331 A | 1/1999 | Anand et al. |
| 5,877,732 A | 3/1999 | Ziarati |
| 6,430,431 B1 * | 8/2002 | De Yoe ..................... 600/410 |
| 7,526,330 B1 * | 4/2009 | Randell et al. ............ 600/421 |
| 2002/0163499 A1 | 11/2002 | Sauer |
| 2005/0273000 A1 * | 12/2005 | Dinehart et al. .......... 600/410 |

OTHER PUBLICATIONS

English abstract of DE 3844482 dated Feb. 1, 1990.

\* cited by examiner

MRI COMPATIBLE VISUAL SYSTEM THAT PROVIDES HIGH RESOLUTION IMAGES IN AN MRI DEVICE

FIELD OF THE INVENTION

The present invention relates generally to those products that are used to provide visual stimuli for testing and comforting patients undergoing diagnostic treatment. More specifically, the present invention relates to an apparatus for providing high resolution images to patients positioned in a magnetic resonance imaging (MRI) device.

BACKGROUND OF INVENTION

In the medical field, magnetic resonance imaging (MRI) is a commonly used non-invasive technique to diagnose the medical condition of a patient. MRI has the ability to distinguish healthy and diseased tissue, fat and muscle, and between adjacent structures within the body which other imaging modalities cannot demonstrate. MRI utilizes safe radio waves and a magnetic field to generate the images processed by a computer. Typically, the patient is placed within a large homogeneous magnetic field and is subjected to a set of gradient fields and radio frequency (RF) fields. The various fields are accurately controlled to cause nuclei within a selected slice of the patient to precess about an axis and to emit RF signals. These signals are then used to reconstruct an image of the slice. By varying the gradient fields, images of the patient at different slices may be captured. The separate slices can then be combined to form a complete scan of the patient.

Generally, with respect to the use of MRI scanners, video systems are employed for both (a) patient comfort and (b) functional imaging applications. With respect to patient comfort, the concern is directed to anxious or claustrophobic patients who resist entering the tunnel of the MRI scanner. The capability to adequately display visual information for viewing is an important factor for relief for the anxious or claustrophobic patient. The second use of video systems in MRI scanners is directed to functional imaging applications. In some instances, the diagnostic procedure performed with the MRI is used to evaluate a patient's response to specific visual stimuli. The operator sends a series of images to a screen which is seen by the patient during the MRI procedure and the patient's responses are included in the MRI report.

A problem with introducing conventional video signals into an MRI device is that very small magnetic fields generated by another device can destroy the images generated by the MRI device. Conversely, the strong fields generated by the MRI device may prevent the normal operation of certain devices, such as a cathode ray tube (CRT) or liquid display panel (LCD), within the vicinity of the MRI device. Therefore, any type of system used to present video signals to the patient must not generate any stray magnetic fields in the vicinity of the MRI device and should be shielded from the magnetic fields generated by the MRI device.

Another problem is that the MRI device is based on the use of radio frequencies that may disrupt signal modulation. For these reasons, the video signal must be in a form that is not affected by the radio frequency and transmitted by a system that is not easily magnetized.

The most common method for presentation of visual stimuli inside the MR scanner is to generate an image outside the magnetic field of the MR machine and have a mirror or prism for reflecting the image to the patient. For instance, viewing systems as described in U.S. Pat. No. 5,076,275 to Bechor et al., U.S. Pat. No. 6,774,929 to Kopp and an MRI video system disclosed in a Nuclear Associates brochure all reflect images generated from a video source located away from the patient into the eyes of the patient. The projection is achieved within the magnetic environment by employing an MRI-compatible LCD screen, or by using a video projector and a translucent screen. The screen is positioned in the proximity of the MR scanner. The projector or LCD screen is positioned either inside or outside the MR room. The video information is viewed by the patient with the aid of adjustable light reflecting mirrors or through a prism. The utility of this method of visual activation is limited by the position of the patient within the scanner tunnel. Further, the level of ambient light in the MRI magnet room will affect the quality of the image that the patient sees on the screen. A high level of ambient light will cause the screen image to be washed out. Also, the time required to adjust the light reflecting mirrors with respect to the screen is determined by the position of the patient inside the scanner tunnel. For functional magnetic resonance imaging, it is ideal to cover the entire patient field-of-view with the MRI screen or display.

The effectiveness of this method of visual activation is further reduced by an open field of view (e.g., the screen is outside of the tunnel) which enables the patient to be aware of her surroundings. Therefore, the patient may find it difficult to focus on the video images and may therefore find it difficult to completely relax. This may be especially true for systems which reflect the video images from behind the MRI device to the patient. With this type of system, the patient may be distracted by items which are adjacent to the display screen or by people working behind the patient. Thus, the possibility of being distracted by the external surroundings in addition to the interior of the tunnel further limits the usefulness of this technique for the reduction of anxiety and claustrophobia in patients. It would therefore be desirable to have the patient focus on the video images during the MRI procedure so that the patient is able to relax.

An attempt to address this problem is found in U.S. Pat. No. 4,901,141 which utilizes a fibre optic taper positioned within the bore of an MRI apparatus. In order to isolate the video system from the fields generated by the MRI device and to prevent any magnetic fields from affecting the MRI device, this system pipes in video images to the patient while the patient is within the MRI device. A CRT produced image is delivered to the fibre optic taper through a coherent image guide. The fibre optic taper expands the end of the image guide so as to provide a larger viewing surface for the patient. The problem with the fibre optic taper is that it is stationary and the patient must be positioned in a fixed location so as to be able to see the end of the optic taper. Further, to prevent distortion the patient must be located directly beneath the isocenter of the taper. Thus, the disclosure does not address different size patients, patient positioning, or near and far sighted patients. For instance, a tall person may lay with their head partially outside the bore during diagnostics of the lower body whereas a child may be well encapsulated by the bore, neither of which could properly see a fixed fibre optic taper. In addition; the use of a fixed taper will interfere with auxiliary coils, such as head and c-spine coils, that require close proximate to the body. Current construction of head and c-spine coils is such that the visual field as needed for viewing a fixed positioned fibre taper is either obscured or completely blocked if the fibre taper is utilized.

Another prior art device is disclosed in U.S. Pat. No. 5,414,459 directed to a pair of glasses worn by the patient. The glasses receive the video picture by fibre optic guide.

In both theses devices the installation is permanent with a fibre optic connection between the shielded MRI room and a remote location housing the operating elements of the system. The connection requires the shielding which surrounds the MRI room to be breeched and that penetration must be adequately protected.

Current MRI fibre optic systems that position the LCD screen within the scanner room (but outside the bore of the MRI scanner) are extremely useful and provide a definite advance in the art. Notwithstanding, certain features of this design could be improved. In particular, the length of the fibre optic bundle employed to carry the video images from the LCD screen to the eyepiece for viewing by the patient is of concern. As with all transmission systems, a portion of the transmitted parameter is lost during transmission and the longer the transmission path, the greater the loss. For long fibre optic bundles, it is known that the loss of as much as forty percent (40%) of the transmitted video image can occur. This loss affects the resolution and brightness of the transmitted video image. Therefore, the resolution and brightness of the transmitted video image is limited by the length of the fibre optic bundle. Additionally, the longer the fibre optic bundle, the more cumbersome it is to carry the bundle and associated fibre optic equipment into and out of the MRI scanner tunnel.

A fibre optic bundle is comprised of a plurality of optical fibres. When an optical fibre is interrupted, the pixels of light of the transmitted image carried by the interrupted fibre are blocked. This situation results in dead pixels, e.g., black spots that appear on the video display. As the length of the fibre optic bundle is increased, the probability that individual fibres will be broken increases. Further, as the fibre optic bundle is bent and manipulated over a period of time, the number of broken fibres increases. An increasing number of broken fibres results in a greater number of black spots appearing on the video display. Eventually, the transmitted image becomes inadequate and distorted. Thus, long fibre optic bundles are not cost effective.

During an MRI examination, the patient is positioned upon an examination table which can be moved into and out of the MRI scanner tunnel. When lying upon the examination table within the scanner tunnel, the patient's head is positioned within a head coil. The head coil is arranged to surround the patient's head and to provide MRI images thereof. An advanced design of MRI scanner head coils minimizes the distance between the patient's eyes and the top of the head coil. The limited distance between the patient's head and the head coil would be inadequate to accommodate the goggles employed by known MRI fibre optic systems that (a) position the image from the LCD display within the scanner tunnel or (b) employ a reflecting mirror over the patient's eyes.

The advance of the functional imaging field requires implementation of visual activation paradigms that are becoming more sophisticated. During functional imaging, the best results are achieved when the visual stimulus is controlled which is inconsistent with an open field of view. Further, this method of visual activation does not include the ability to generate three-dimensional (3D) images for patient viewing since the image is projected onto a single screen. The inability to create a condition is which the eye and brain perceive a 3D effect prevents virtual reality from being achieved.

Further, the development of new and smaller head coils limits the distance between the patient's head and the head coil, putting restraints on the size of the goggles to be used within the head coil. Together with the introduction of MR machines with higher field strength both in the clinical and research field, the shielding of the MR goggles to avoid generation of any stray magnetic fields or disruption of signal modulation by radio frequency is becoming increasingly important.

The use of functional imaging in clinical work also requires devices that are fast and easy to set up and operate in a tight clinical schedule. Easy positioning of the device and effective eye correction features are crucial elements to achieve a satisfactory clinical workflow.

Thus, there is a need in the art for an improvement in video systems for use with MRI scanners which provide high resolution video images with a three-dimensional effect, shortens the transmission paths that the video image must travel, eliminates the problems associated with fibre optic bundles, is sized to fit within the limited space of modern head coil designs, is sufficiently shielded to avoid image artefacts and can be mounted and operated within the MRI magnetic field.

SUMMARY

According to the present invention, the above mentioned improvements are solved by means of an apparatus according to the characterizing clauses of claims 1 and 6. Further preferred embodiments and improvements are obtained by the features given in the dependent claims.

DETAILED DESCRIPTION OF THE INVENTION

The following detailed description outlines an MRI compatible visual system having a head coil mounted micro display. In the following description, numerous details such as specific materials and configurations are set forth in order to provide a more complete understanding of the present invention. But it is understood by those skilled in the art that the present invention can be practiced without these specific details. In other instances, well known elements are not described in detail so as not to obscure the present invention. In any event, the scope of the invention is best determined by reference to the appended claims.

General Arrangement

Figure 1:
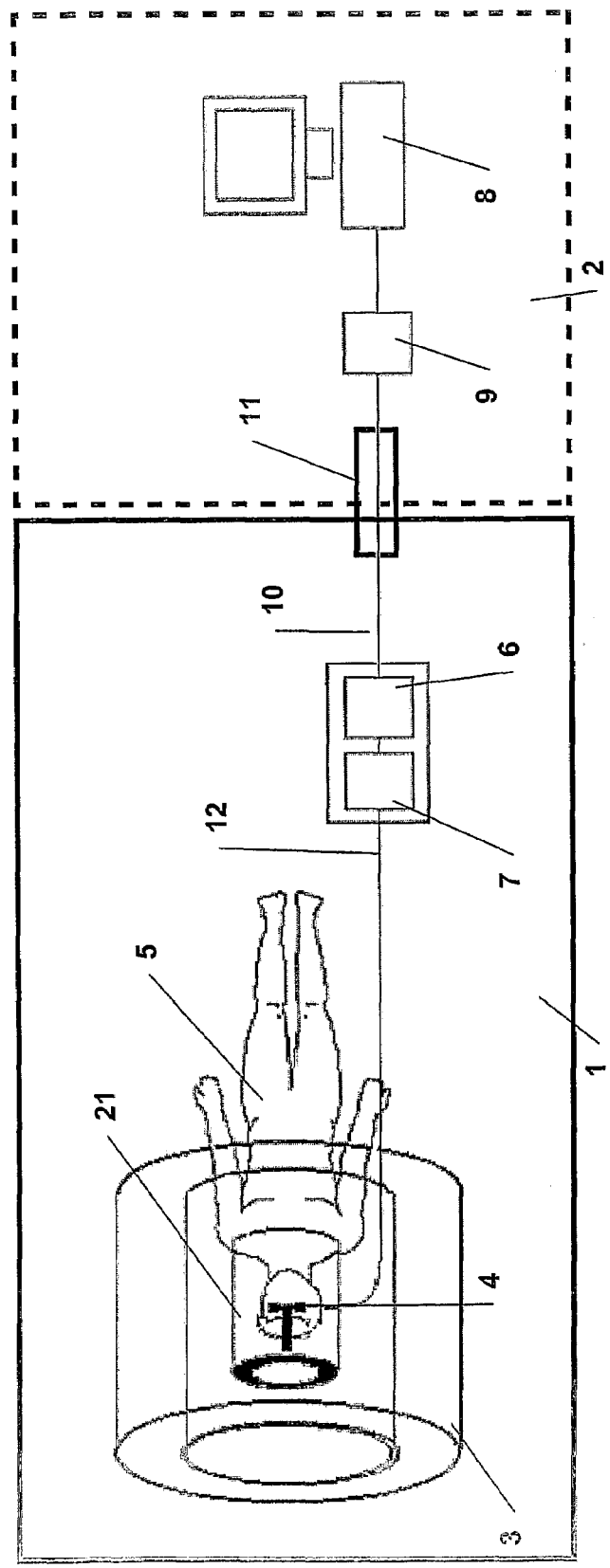
FIG. 1 is a view of a preferred embodiment of the present invention illustrating the entire visual system separated between a control room and a magnet room.

In a preferred embodiment, the present invention provides an MRI compatible visual system. FIG. 1 gives a general overview of how the present invention system is set up in relation to the MRI system, which is disposed partly in a magnet room 1 and partly in a control room 2.

One portion of the present invention system is located inside the MRI control room 2. That portion of the system includes a fibre optical transmitter 9. The control room 2 also contains a PC 8. Dashed lines in FIG. 1 circumscribe the borders of that room. Everything outside the dashed lines represents the examination or magnet room 1. The other portion of the system that includes a head coil mounted micro display and its circuitry are located within the magnet room 1. As the name implies, the magnet room 1 contains a main magnet 3 of the MRI device that generates a strong magnetic field.

Continuing with the general overview, FIG. 1 shows that the system contained in the magnet room 1 is again divided such that certain parts of the system are mounted inside the bore of the main magnet and other parts remain outside the bore. The parts inside the bore include adjustable head coil mounted micro displays 4. Outside the bore, but still inside the magnet room 1 includes fibre optical receiver unit 6 and micro display control electronics 7.

Control Room Part

In the control room 2 a fibre optical transmission unit 9 receives signals from a PC 8. The fibre optical transmitter converts electrical signals into light signals. A fibre optic cable 10 is used to bring the light signal into the magnet room 1. The fibre cable 10 is mounted via a wave guide 11. A typical MRI signal is very sensitive to the electrical noise around the procession frequency of a hydrogen proton, wherein this frequency varies from 12 MHz to 130 MHz depending on the field strength of the magnet. This relationship is generally expressed as:

$$f=42.5*B$$

wherein B is the field strength in Tesla and f is the frequency in Megahertz.

Mindful of the foregoing relationship, the dimensions of the wave guide is calculated so that only non-disturbing frequencies will enter the magnet room. The wave guide 11 is typically a tube mounted on the Faraday cage that surrounds the magnet room (not shown).

Magnet Room Part

Figure 5:
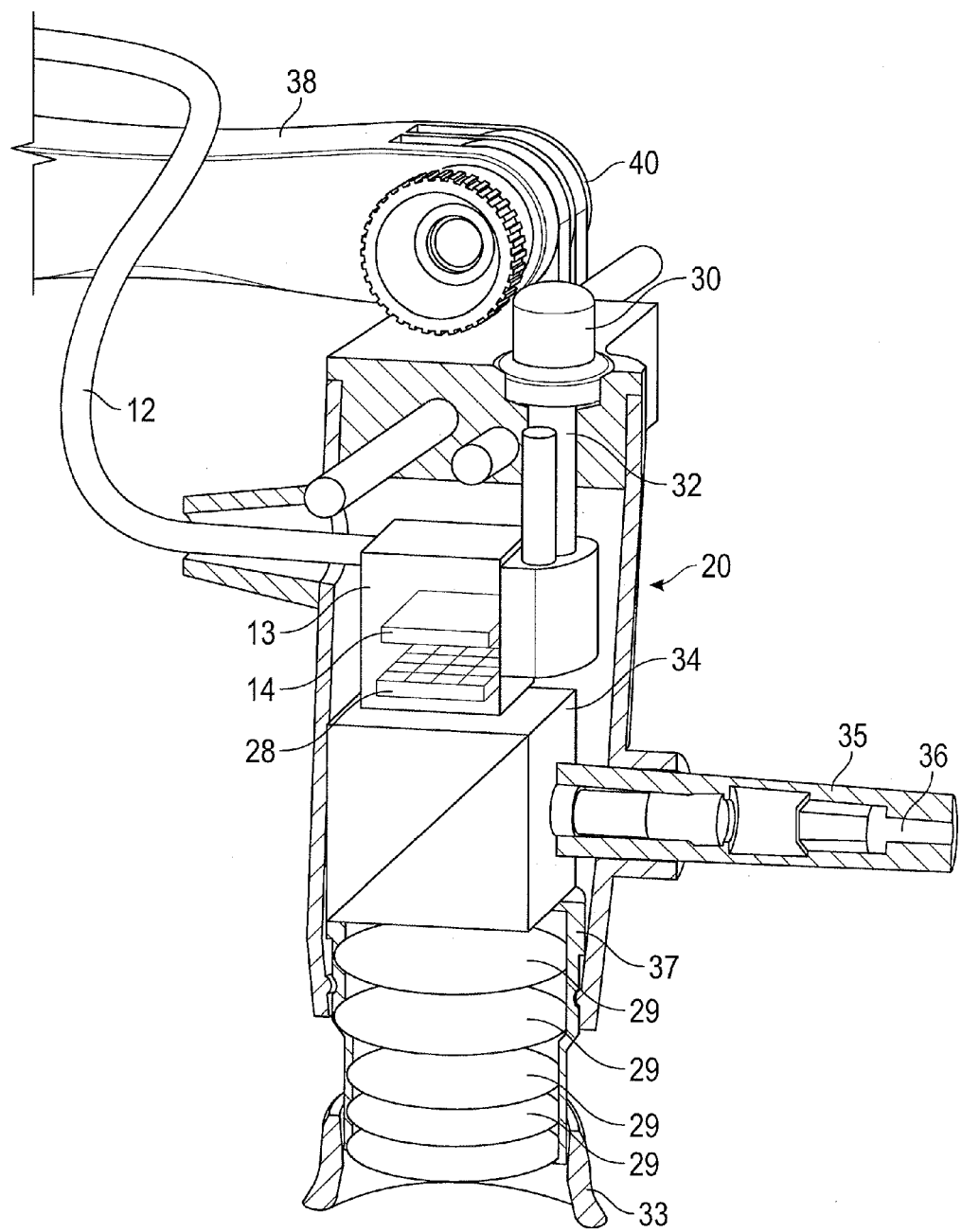
FIG. 5 is an exploded view of the arrangement of the micro display housing.

The fibre optic cable 10 is fed into the magnet room 1 where the other part of the visual system is located. In the magnet room 1 there is a fibre optic receiver unit 6. This converts the light signals into electrical signals. The signals enter a micro display driver unit 7. This unit controls the micro display chips 14 (FIG. 5) and controls image rotation, colour adjustments, automatic shut down and other functions.

Figure 2:
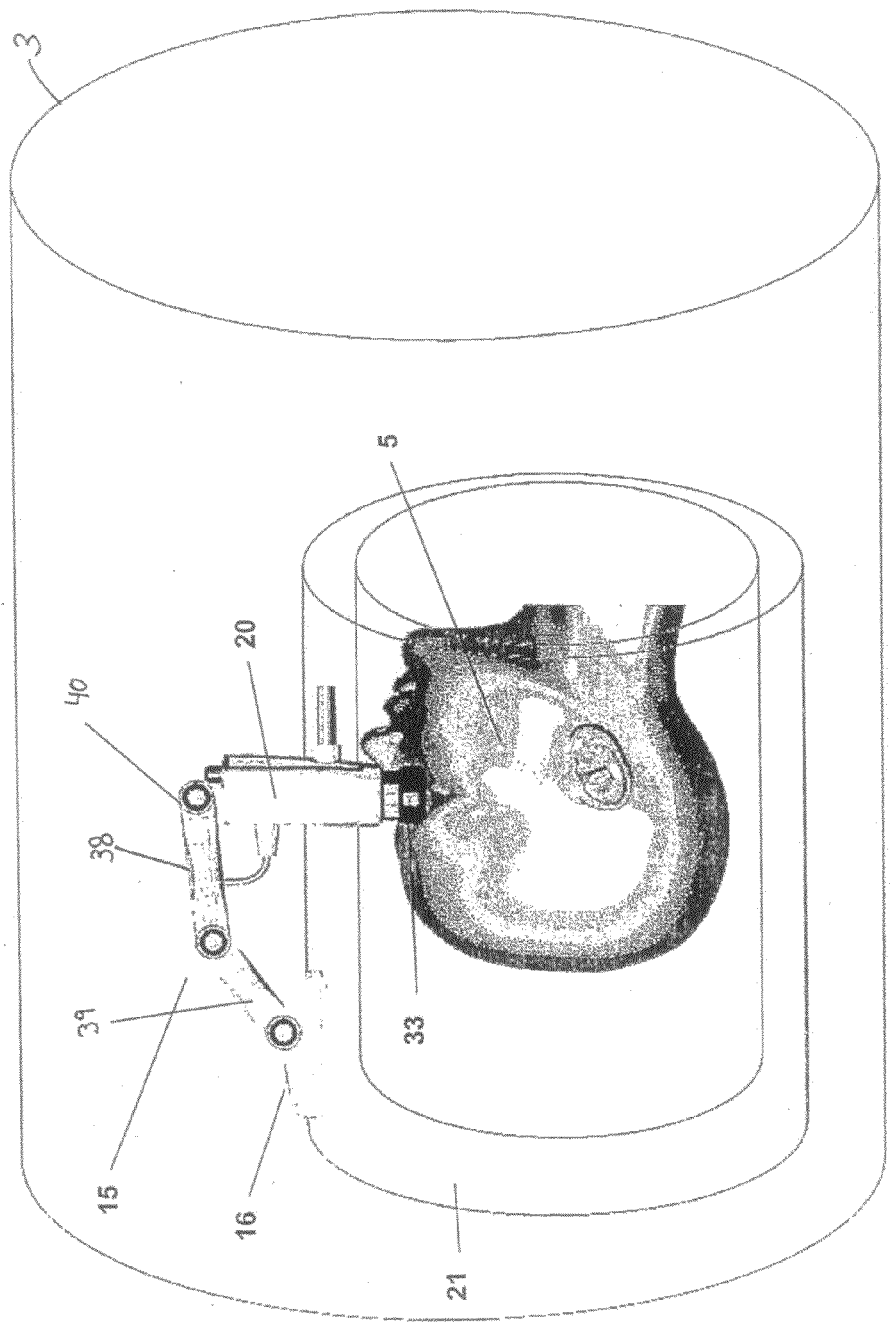
FIG. 2 is a view of a preferred embodiment of the visual system showed used in a MRI system bore.

The micro display chips are mounted on an adjustable arm 15 (FIG. 2). The mechanism is designed to make it easy for the patient 5 to adjust the visual system into the right angle for preferred view.

Between the micro display driver unit 7 and the micro display chips 14 there are a shielded cable 12. The shielded cable 12 brings the electrical signals into a small faradays cage 13 (FIG. 5) that contains the micro display 14.

Adjustment of the Micro Display Housing.

Main Viewing Angle Adjustment

Figure 4:
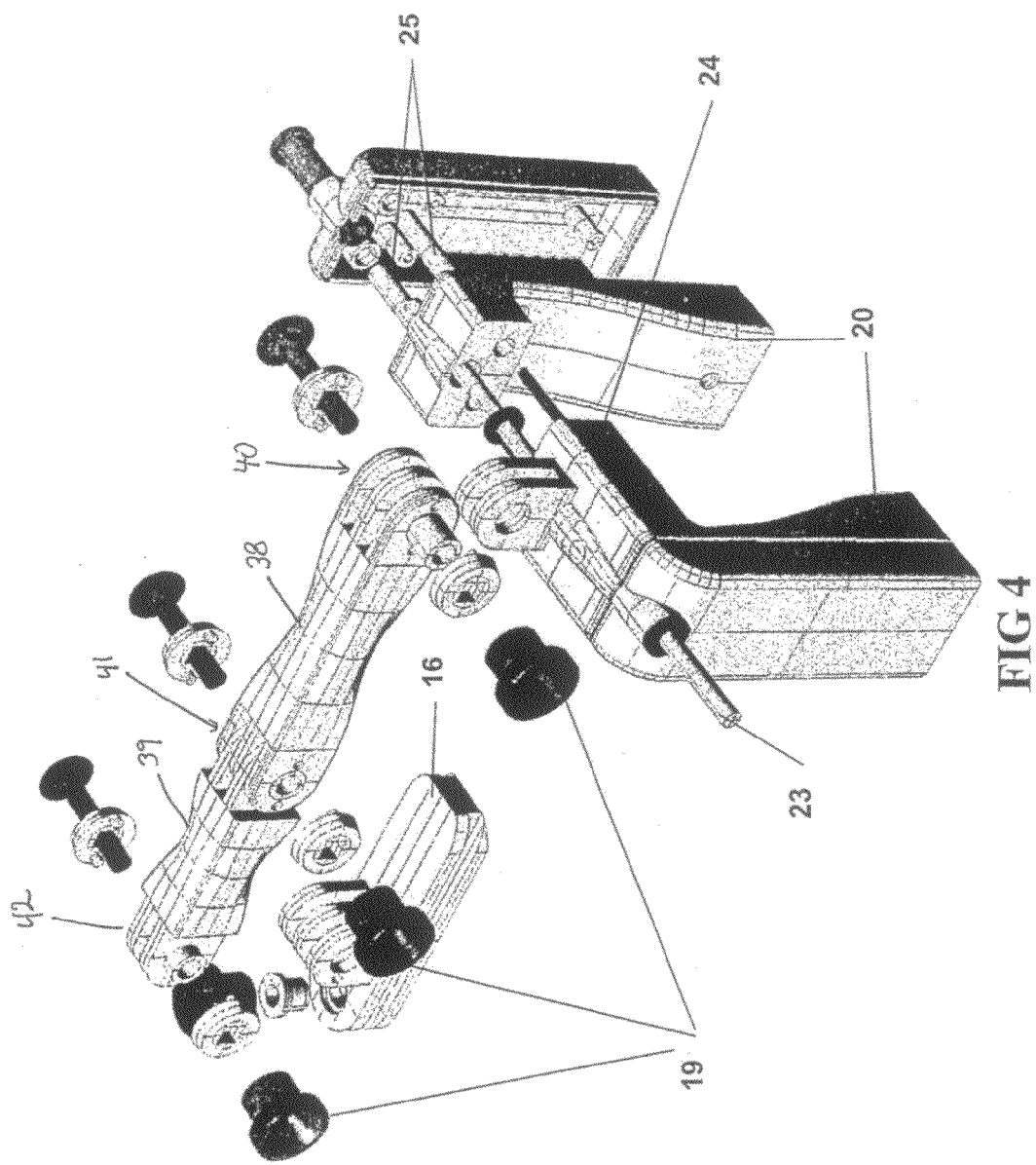
FIG. 4 is a view of the adjustment arm and pupil distance adjuster

FIG. 2 illustrates the adjustment mechanism on the head coil mounted micro display 4. The mechanism consists of a coil attachment part 16 two distance arms 38, 39 with friction links 40, 41, 42 and friction adjustment knobs 19 (FIG. 4).

Figure 3:
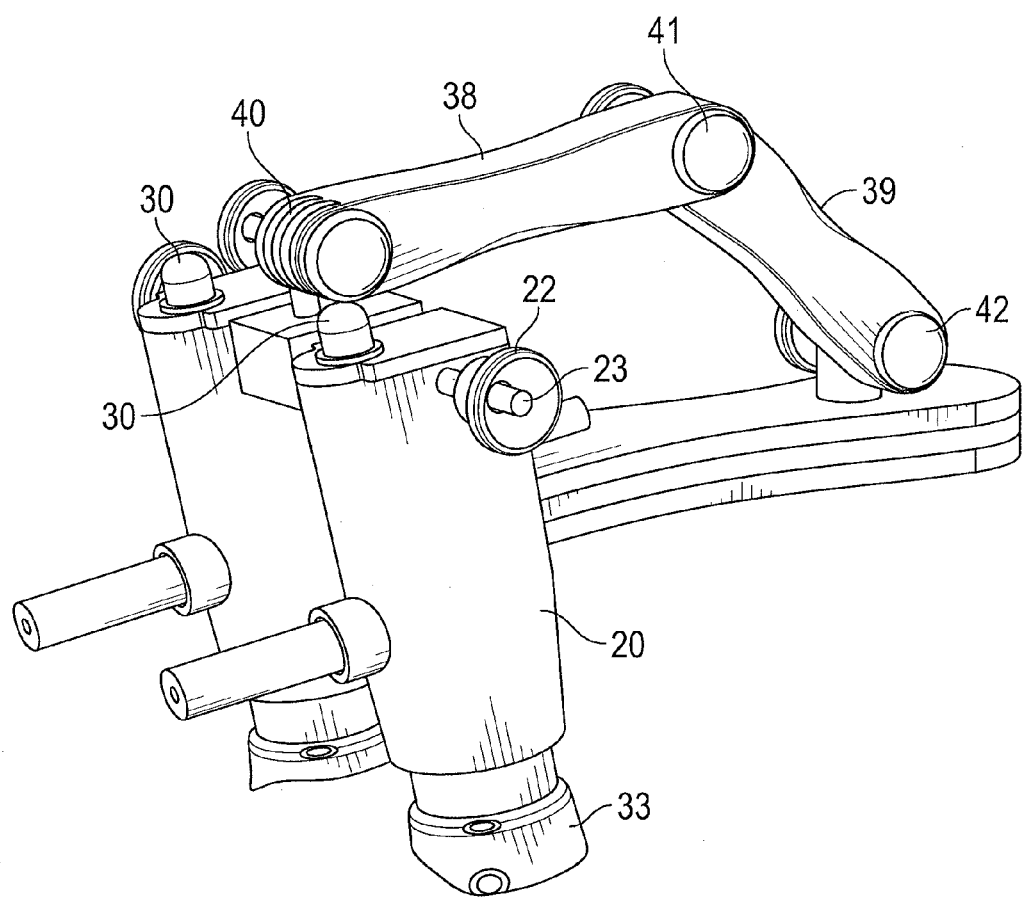
FIG. 3 is a view of a preferred embodiment of the visual system showing the adjustable arm, the housing of the micro displays chip and optics, the pupil distance adjustment knob and the dioptic compensator knobs.

The adjustable arm allows people lying in different positions in the head coil to have a quick adjustment to get the micro display housing 20 (FIG. 3) in the right position for best angle of view. The distance arms 38, 39 in combination with the friction links 40, 41, 42 let the micro display housing 20 move both in horizontal and vertical direction. The angle of the micro display housing 20 can also be changed. The coil attachment element 16 is arranged to fit different head coils 21. The system is arranged to fit several different kinds of coil attachment elements 16, thereby facilitating fitment in different head coil systems.

Pupil Distance Adjustment Mechanism.

According to the present invention, the system has adjustments for pupil distance. The distance is adjusted by turning knob 22. The knob 22 will move the micro display housing 20 symmetrical away from and against each other.

The knob 22 is fixed to a shaft 23. The shaft can rotate inside the mid section 24. The movement of the micro display housings 20 is fixed into one direction with two bolts 25. The shaft 23 is threaded with opposite threads on each side of mid section 24. Turning the shaft 23 will make a symmetrical movement on the micro display housings 20.

Micro Display Housing Arrangement

The micro display chips 14 are mounted and fixed inside Faraday cages 13 mounted in the micro display housings 20. The Faraday cages 13 shield the sensitive electronics against disturbances generated by the RF pulses from the scanner 3. The Faraday cages 13 also shield against electromagnetic noise generated by the micro display 14. In the lover part of the Faraday cage 13, there is arranged a shielded window 28. The shielded window 28 comprises wires or a mesh of metal that keeps the shielding function intact, but also let the patient 5 see the image on the micro display 14.

Between the patient's eye and the micro display there are arranged optical elements 29 that enlarge the image from the micro display 14. The optical elements 29 are designed so the micro display 14 is mounted a couple of centimeters away from the patient's eye. The design of the optical elements decreases the problem of distortion on the MRI system caused by the electronics and display chip 14.

The knob 30 facilitates dioptic correction for patients that normally wear glasses. Adjusting the knob 30 will change the distance between the micro display 14 and the optical elements 29. The motion of the Faraday cage 13 is locked into one direction by two bolts 31. The Faraday cage 13 is threaded inside. The knob 30 is fixed to the end of a shaft 32. The shaft 32 is threaded, and by turning the knob 30, the Faraday cage will slide along the bars 31. The micro display 14 is fixed inside the Faraday cage 13, thereby ensuring that the movement of the micro display 14 will equal to the movement of the Faraday cage 13. The optical elements 29 are arranged to ensure that a linear movement of the micro display 14 will result a dioptic correction that follows the normal steps used in the dioptic scale. For example, turning the knob 30 half a turn may give an adjustment of one step on the dioptic scale.

Around the housing of the optical elements 37 there are softer materials 33 that will cover the patient's eye completely. The cover avoids the patient to be disturbed by ambient light.

As a part of the optical system there is mounted a beam splitter. The beam splitter is designed to let the visible light pass, but the light in the infra red frequency area is led into another optical direction, the eye tracker channel 35. The beam splitter allows an infrared image of the patient's eye to enter the eye tracker channel 35. The image of the patient eye is fed into the end of a coherent image guide 36. In the other end of the coherent image guide 36, it is possible to connect an infrared camera to capture the movement of the patient's gaze. To ensure a crisp and bright image in the infrared camera end of the coherent image guide, the patient's eye is lit up with infrared light. This infrared light is fed into the magnet bore by one or more fibre optic cables (not shown).

The invention claimed is:

1. An MRI compatible visual system wherein the MRI compatible visual system comprises:
   a head coil, the head coil being adapted to surround a patient's head;

an adjustment mechanism comprising a coil attachment part mounted onto the outside of the head coil, a first extended member connected to the attachment part with friction link in a first joint, a second extended member connected to the first member with friction link in a second joint or joints where the second joint is at the opposite end of the first joint, and the second extended member is at its end opposite of the second joint or joints also connected to a housing with friction link in a third joint, wherein each joint is hinged to allow rotation of the joints, and where a longitudinal direction of the housing stretches from the first joint to a distal end of the housing;

said housing further comprising:

an adjusting knob positioned at the top of the housing adjacent to the third joint, the adjustment knob being fixed to one end of a shaft inside the housing and the shaft is at the other end fixed to a small Faraday cage inside the housing enabling a linear movement of the Faraday cage in the longitudinal direction of the housing;

the Faraday cage contains a micro display chip for receiving video or picture image signals from an external source, and the micro display chip converts a video or picture image signal to a visible image on a small screen so as to provide high resolution images to patients positioned in the magnetic resonance imaging (MRI) device;

the Faraday cage comprises a shielded window positioned below the micro display ship closer to the distal end of the housing wherein the shielded window is covered by wires or a mesh of metal that keeps a shielding function intact, a connection to a shielded cable connected to the small Faradays cage inside the housing;

a beam splitter adjacent to the Faraday cage and closer to the distal end of the housing than the Faraday cage, wherein the beam splitter enables an image of a patient eye to be fed into the end of a coherent image guide; and optical elements adjacent to the beam splitter and closer to the distal end of the housing than the beam splitter, wherein the optical elements adjustably enlarge the image from the micro display chip.

2. The system according to claim 1, wherein the distance between the Faraday cage and the optical elements in a lower part of the housing is such that no sensitive or disturbing electronic parts are located inside the head coil during operation of the MRI device, while the part of the housing that is inside the head coil during the operation of the MRI device only comprises elements that do not significantly affect the MRI and are not significantly affected by the magnetic and RF fields inside the head coil.

3. The system according to claim 2, wherein the housing comprises two optical apertures, the distance between said optical apertures being adjustable.

4. The system according to claim 2, wherein the coil attachment element is adapted to fit different head coils or other parts of the MR1 device.

5. The system according to claim 1, wherein the distance between said optical apertures is adjustable.

6. The system according to claim 5, wherein the coil attachment element is adapted to fit different head coils or other parts of the MRI device.

7. The system according to claim 1, wherein the coil attachment element is adapted to fit different head coils or other parts of the MR1 device.

8. An MRI compatible visual system, wherein the MRI compatible visual system comprises:

a head coil, the head coil being adapted to surround a patient's head;

an adjustment mechanism comprising a coil attachment part mounted onto the outside of the head coil, a first extended member connected to the attachment part with friction link in a first joint, a second extended member connected to the first member with friction link in a second joint or joints where the second joint is at the opposite end of the first joint, and the second extended member is at its end opposite of the second joint or joints also connected to a housing with friction link in a third joint, wherein each joint is hinged to allow rotation of the joints, and where a longitudinal direction of the housing stretches from the first joint to a distal end of the housing;

said housing further comprising:

an adjusting knob positioned at the top of the housing adjacent to the third joint, the adjustment knob being fixed to one end of a shaft inside the housing and the shaft is at the other end fixed to a small Faraday cage inside the housing enabling a linear movement of the Faraday cage in the longitudinal direction of the housing;

the Faraday cage contains a micro display chip for receiving video or picture image signals from an external source, and the micro display chip converts a video or picture image signal to a visible image on a small screen so as to provide high resolution images to patients positioned in the magnetic resonance imaging (MRI) device;

the Faraday cage comprises a shielded window positioned below the micro display ship closer to the distal end of the housing wherein the shielded window is covered by wires or a mesh of metal that keeps a shielding function intact, a connection to a shielded cable connected to the small Faradays cage inside the housing;

a beam splitter adjacent to the Faraday cage and closer to the distal end of the housing than the Faraday cage, wherein the beam splitter enables an image of a patient eye to be fed into the end of a coherent image guide;

optical elements adjacent to the beam splitter and closer to the distal end of the housing where the optical elements adjustably enlarge the image from the micro display chip; and a pupil distance adjustment mechanism provided by pupil adjustment knobs fixed to a shaft, wherein the adjustment knobs located on the outside of the housing proximate to the third joint, the shaft can rotate inside a mid section of the part of the housing close to the third joint, the movement of the housing is fixed in the longitudinal direction of the housing with two bolts, the shaft is threaded with opposite threads on each side of the mid section, and turning the shaft gives a linear movement of the housings in the longitudinal direction of the housing.

9. The system according to claim 8, wherein the distance between the Faraday cage and the optical elements in a lower part of the housing is such that no sensitive or disturbing electronic parts are located inside the head coil during operation of the MRI device, while the part of the housing that is inside the head coil during the operation of the MRI device only comprises elements that do not significantly affect the MRI and are not significantly affected by the magnetic and RF fields inside the head coil.

10. The system according to claim 9, wherein the housing comprises two optical apertures, the distance between said optical apertures being adjustable.

11. The system according to claim 9, wherein the coil attachment element is adapted to fit different head coils or other parts of the MRI device.

12. The system according to claim 8, wherein the distance between said optical apertures is adjustable.

13. The system according to claim 12, wherein the coil attachment element is adapted to fit different head coils or other parts of the MRI device.

14. The system according to claim 8, wherein the coil attachment element is adapted to fit different head coils or other parts of the MRI device.

* * * * *